May 28, 1968 M. J. MURRAY Plant Pat. 2,811
MINT STRAIN
Filed Sept. 27, 1966
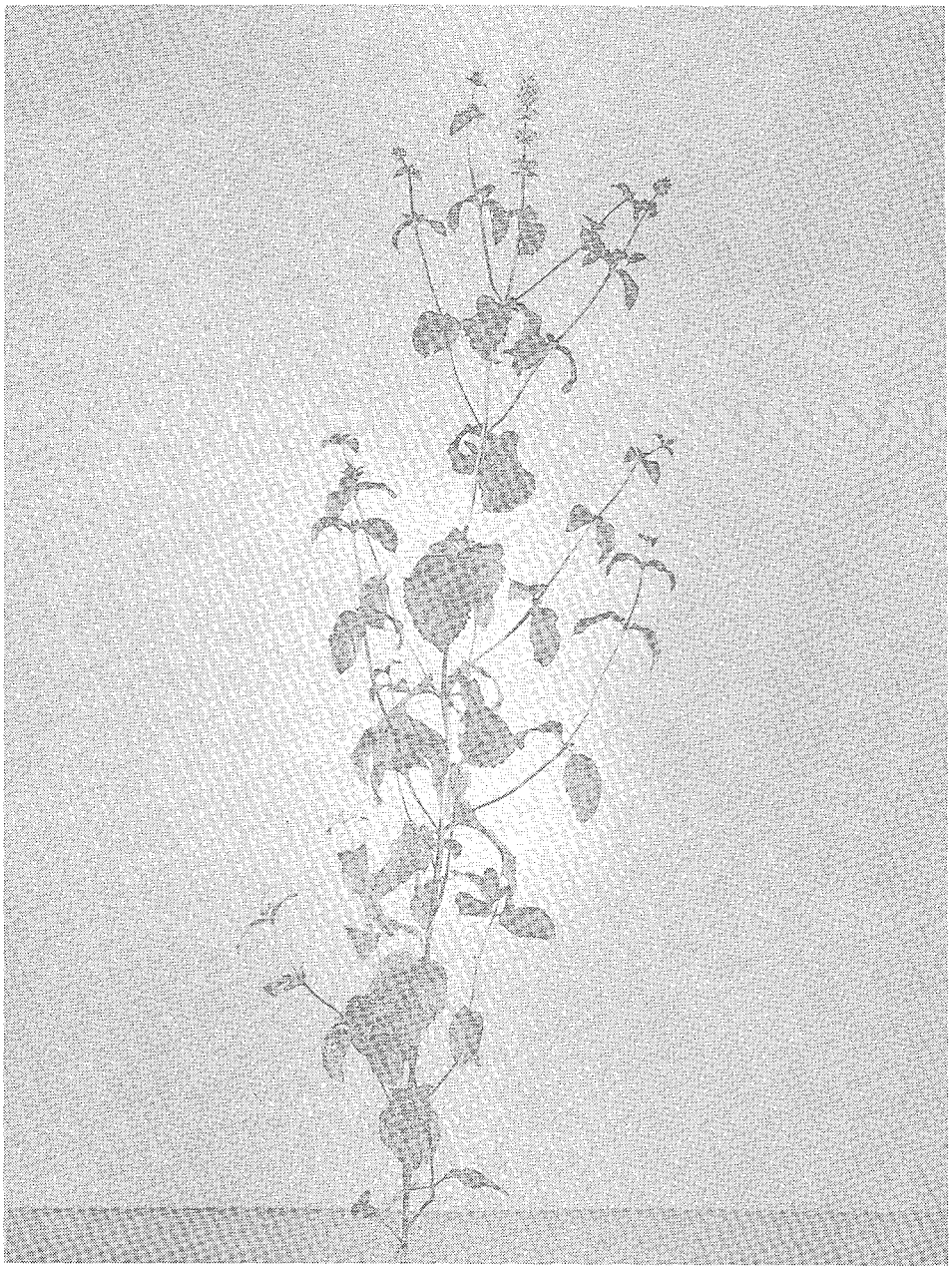
INVENTOR
MERRITT J. MURRAY
Huesches and Kurlandsky
ATTORNEYS United States Patent Office Plant Pat. 2,811
Patented May 28, 1968

2,811
MINT STRAIN

Merritt J. Murray, Kalamazoo, Mich., assignor to A. M. Todd Company, Kalamazoo, Mich., a corporation of Michigan Filed Sept. 27, 1966, Ser. No. 582,465
1 Claim. (Cl. Plt.—89)

This invention relates to a new and distinct variety of mint plant which was originally produced by hybridizing a clonal strain (European origin unknown) of diploid *Mentha citrata* Ehrh. (which is male sterile) as a seed parent to a pollen parent (59–242) which was a menthone-odored, highly wilt-resistant selection which had been derived previously from hybridizing diploid *Mentha crispa L.* (also taxonomically known as *Mentha spicata* L. var. *crispata*) to a colchicine-induced tetraploid strain of *Mentha longifolia* (L.) Huds. (also known as *Mentha sylvestris* L.).

The novel mint strain of the invention is an early maturing plant having small-sized, veiny and rolled but not really crisp, thick leaves, and having excellent stolons which over-winter well. The new variety has very distinctive sage-like odor characteristics and very pronounced winter-hardiness as compared to the *Mentha citrata* parent.

In the drawing, which is a photographic illustration of the new variety, the figure is a view of the plant showing the general form of the stems, leaves, and flowers.

The male parent (59–242) used in the cross was derived from a cross made in 1950 and seedlings grown in 1951 as 51–1266. These first generation hybrids between *Mentha crispa* and tetraploid *M. sylvestris* are perfectly fertile, and our specific selection had a menthone odor and very crisp, lacerate leaves. It was not susceptible tc rust and was selected for its high wilt resistance and vigorous growth. Disease resistance and vigor were confirmed through tests of the clonal strain over the nine-year period 1951–1959.

The hybridization of *Mentha citrata* and 59–242 was accomplished in the summer of 1960. Seedlings were first grown in 1961 and 18 of the seedlings were planted in a western nursery (eastern Oregon). At harvest time, the most vigorous seedling was assigned the harvest number 61–719 and its herbage was harvested and distilled for odor evaluation and chemical assay by vapor chromatography.

This strain was first vegetatively propagated in April 1962. Its oil quality and yield and disease resistance were studied in this 1962 plot, and subsequently in a further plot in 1963. A large plot was planted in late May of 1963 from plants grown in a Kalamazoo, Mich. greenhouse to expedite the stolon increase of this strain. The strain was further studied in a larger plot in 1964 and from the second-year growth of this plot in 1965. A large planting of this strain was undertaken in 1965 primarily for the production of stolons. The new strain shows excellent growth and resistance characteristics when grown in Idaho and Oregon.

*Mentha citrata* Ehrh. has a pleasant odor which is due to the fact that the oil has a high linalool and high linalyl acetate content. An oil of this sort would be of some commercial interest, but unfortunately *Mentha citrata* is not adapted to the U.S. climatic conditions present in our normal mint-growing areas. Its lack of adaptation in northern mint-growing areas favorable to the growth of mint plants as represented by *Mentha piperita* L. is indicated by its low yield (seldom more than 30 lbs. per acre), and by its general lack of winter hardiness (frequently freezes out over winter). It is also short in height and lacking in vigor. *Mentha citrata* often produces short or almost no stolons. As a result, the second-year stand is frequently skimpy and requires much replanting. It would appear from these observations that the native strains of *Mentha citrata* were adapted to a more southern, or at least a milder, climatic region along the Mediterranean from which they apparently came. My general plant breeding objectives were to improve the adaptation of *M. citrata* and to obtain a plant with good stolons that would over-winter, and the novel mint strain of the invention satisfies these objectives and additionally has very distinctive characteristic odors that are of interest to perfumers in compounding perfumes.

The novel Plot 1 strain of the invention is intermediate in appearance between the parental strains, but is readily distinguishable from either of the parents.

(A) *Differences between male parent and Plot 1*

The new variety is distinguished from its male parent by its chemical composition, since Plot 1 has about 35% linalyl acetate and 53% linalool and no appreciable menthone or menthol content. In the genus Mentha, these acyclic, or chain, compounds are found in quantity only in *Mentha citrata* and in certain hybrids derived from it, where as the male parent has menthone, a cyclic compound, as the principal ketone. The male parent has no appreciable amount of either linalyl acetate or linalool, nor does either of the parental species (*M. crispa* or *M. longifolia*) which gave the hybrid which was used as the male parent in the present cross.

From a morphological point of view, the *Mentha crispa* × *M. longifolia* hybrid, or male parent, is easily distinguished, since it has a *Mentha spicata*-like appearance and has very crisp leaves with incised lacerate margins and dentate teeth, a very coarse stem and very erect habit, compared to the almost flat leaves, serrate teeth and branched loppy habit of the new hybrid. The male parent has slender and narrowly elongate acute terminal flower spikes with the individual flower clusters usually subtended by small bracts, whereas the new variety has openly spaced, capitate glomerules in obtuse ovoid spikes which are essentially terminal with a few flower clusters sub-axillary and all flower heads subtended by small-sized leaves. The male parent is thus very different from either the Plot 1 hybrid or *Mentha citrata* for neither have crisp leaves with lacerate-incised margins or bear any close resemblance to *M. spicata*.

(B) *Differences between* Mentha citrata *and Plot 1*

*Height.*—The Plot 1 strain is 23–28″ tall where erect, but it frequently lops or falls over to a height of 17–20″, whereas the unadapted *Mentha citrata* strain is usually 12–15″ tall even under good growing conditions.

*Plant habit.*—The hybrid is much more vigorous and the stems are much more branched than the *Mentha citrata* parent. The hybrid strain is therefore much more leafy with medium-sized leaves on the main axis and small sized-ones on the secondary branches. It is more leafy due to numerous fine branches that bear leaves.

*Plant stems.*—The *Mentha citrata* parent has coarser, more fragile stems that tend to split rather than bend, whereas the hybrid has more slender stems which bend and lop when the plant becomes tall and top heavy.

*Maturity.*—The new hybrid grows faster and is usually earlier in maturity. In the hybrid the flowers are sometimes gone by September 10th, where as those of the parental *citrata* are just beginning to open. The meadowmint or second year crop of Plot 1 in 1965 had 98% of the flowers past on the first of September.

*Yield.*—The yield of the Plot 1 hybrid is almost double that of the *Mentha citrata* parent. As mentioned previously, the *Mentha citrata* parent usually yields around 30–35 lbs. of oil per acre, whereas the first-year yield of Plot 1 was 68 lbs. per acre from a thickly planted 1/50 acre plot.

Furthermore, a one-acre plot yielded 83 lbs. per acre in its second year. This is a far higher yield than has been obtained from the *Mentha citrata* parent, even in its second year (estimated at 40–50 lbs. per acre).

*Leaf shape and size.*—*Mentha citrata* has oval or ovate leaves which are almost as broad as long, generally 1–1½" long, whereas the hybrid has longer leaves, frequently 2¼" long by 1½" wide with the main stem leaves more elliptical in outline, or elliptical-ovate in outline. The uppermost leaves of the hybrid (or those on small branches) are ovate and much smaller, about as broad as long (1").

*Leaf apex.*—The main stem leaves of *Mentha citrata* usually have obtuse or rounded tips whereas those of the hybrid are much sharper and more nearly acute.

*Leaf base.*—The leaf base of *Mentha citrata* is broadly cordate, or heart-shaped, where as that of the hybrid is very narrowly so and much less pronounced. The leaf base of the hybrid could therefore be called sub-cordate.

*Leaf texture.*—The leaves of *Mentha citrata* are coriaceous, or leathery, whereas those of the hybrid are thinner, this difference being more pronounced in greenhouse-grown plants than in field plants.

*Leaf margin.*—The leaf margins of *Mentha citrata* can be described as "sharply oppressed-serrate" with small teeth, whereas the hybrid has its leaf margins similar but with the teeth slightly larger, especially on the younger leaves which are also generally somewhat wrinkled.

*Leaf teeth.*—The serrate teeth of *Mentha citrata* are generally less than one millimeter long on the sharp edge, whereas those of Plot 1 are usually two millimeters long on the sharp edge. Other strains of *Mentha citrata* do have leaf teeth as large as those of Plot 1, but the diploid *M. Citrata* used in our hybridization has small teeth that are not noticeable at a distance of 24". Those of the hybrid are more prominent and conspicuous even to a casual viewer.

*Leaf contour.*—*Mentha citrata* has leathery, or coriaceous, leaves which are almost flat, whereas the main stem leaves of the new hybrid are essentially flat with only a slight twist or a slight degree of crispness. In the hybrid, the smaller leaves on the side branches and especially those near the top of the plant are inclined to be more crisp and to show more strikingly the effects of the male parentage than are the main leaves of the plant. To repeat, the male parent has lacerate, very incised, dentate, and very crisp leaves. While both the hybrid and *Mentha citrata* tend to roll the tip of the mature leaf downward, the surface of the *Mentha citrata* leaf is flat, whereas that of the hybrid may have both side edges tending to point upward at a more or less 45° angle. This is particularly true of the younger leaves but is not invariable.

*Leaf surface.*—The coriaceous leaves of *Mentha citrata* are only slightly wrinkled between the major leaf veins, whereas this wrinkling is much more pronounced in the Plot 1 strain. This wrinkling and the twist that one usually finds in the leaves of Plot 1 are such that it is difficult to press a leaf flat.

*Leaf petiole.*—The petioles of the main stem leaves of *Mentha citrata* are about 13–25 mm., usually about 15 mm. long, whereas those of the hybrid are shorter and generally about 8 mm.

*Leaf color.*—The leaves of the hybrid are a somewhat lighter green with a yellowish cast, whereas those of the *Mentha citrata* strains are generally medium to dark green.

*Flower spikes.*—The flowers of *M. citrata* are in capitate glomerules forming close-spaced ovoid spikes, generally not over 1" long, often with some of the lower flower spikes sub-axillary, whereas the glomerules of the hybrid are generally more openly spaced giving a less compact or dense inflorescence. While a flower cluster or glomerule of *Mentha citrata* and that of the hybrid appear to have about 20 flowers each, the flower clusters of the hybrid are generally less closely spaced. There is no substantial difference in the length of the pedicels to the flowers, both being about 2½ mm. long. The flowers and pedicels are glabrous, without hairs.

*Flower color.*—The flowers of both the hybrid and the parental *M. citrata* strain are lavender in color, although the hybrid generally tends to be slightly lighter.

*Position of flower spikes.*—The flower spikes of both *Mentha citrata* and the hybrid are terminal and only slightly sub-axillary, as compared with various previously patented menthol-producing mint hybrids which have distinctly and definitely axillary flowers.

*Flower spikes subtended by.*—The flower spikes of *Mentha citrata* are subtended by half-size or full-size leaves generally, whereas the hybrid has the flower spikes subtended by small-sized leaves. The leaves near the flower spikes on the hybrid are generally ¼ to ⅓ the size of the main stem leaves. This reduction in leaf size is much more pronounced in the hybrid than it is in most *Mentha citrata* strains.

*Stolons.*—The stolons of the hybrid are much longer and much coarser with a larger diameter than those of the parental *citrata* strain which has very fine short stolons. This difference in stolons relates directly to over-wintering ability. Those of the *Mentha citrata* strain are generally poor and may not over-winter, whereas the hybrid of the invention has excellent stolons and exhibits an excellent survival record over the test period observed, especially under climatic conditions favorable to the growth of mint plants as represented by *Mentha piperita* L.

*Other characteristics in common.*—The *Mentha citrata* parent and the hybrid are alike in having no hairs on the stems, leaves or flowers and in having opposite, decussate leaves, and essentially terminal flowers. The color of the stems and above ground stolons is reddish, this being characteristic of many other mints including *Mentha citrata* which is like the hybrid in this regard.

*Oil composition.*—Based upon a three-year average, the new hybrid contains about 35% linalyl acetate and 53% linalool. Our experience demonstrates that the percentage of these components is variable depending in part upon the maturity of the plant at harvest. It is most prominent for its very fine clary sage-like odor with a very good top-note and a fair dryout and without any minty or hay-like elements. The new variety is particularly distinctive for its clary sage-like odor as compared to *Mentha citrata*, which does not have this odor element to any essential extent.

Propagation and tests were conducted in Kalamazoo, Mich. and eastern Oregon with some of the disease tests in Indiana. The new hybrid was first vegetatively propagated in Oregon in 1962 and has exhibited its hardy characteristics and adaptiveness in both Oregon and Idaho. It has consistently exhibited the foregoing characteristics since the time of its first asexual reproduction from stolons in 1962.

I claim:

1. A new and distinct variety of mint plant substantially as herein shown and described, characterized particularly by its clary sage-like aroma, its hardy characteristics under climatic conditions favorable to the growth of mint plants as represented by *Mentha piperita* L., vigorous winter-hardy stolons which are thicker and longer as compared with those of *Mentha citrata* Ehrh., and having as major components linalyl acetate and linalool and no substantial menthone or menthol content.

No references cited.

ROBERT E. BAGWILL, *Primary Examiner*.